United States Patent [19]

Abichandani et al.

[11] Patent Number: 5,689,027
[45] Date of Patent: *Nov. 18, 1997

[54] SELECTIVE ETHYLBENZENE CONVERSION

[75] Inventors: Jeevan S. Abichandani, Voorhees; Jeffrey S. Beck, Lawrenceville; David H. Olson, Pennington; P. Thomas Reischman, Lambertville; David L. Stern, Lawrenceville; Chaya R. Venkat, Princeton, all of N.J.

[73] Assignee: Mobil Oil Corporation, Fairfax, Va.

[ * ] Notice: The term of this patent shall not extend beyond the expiration date of Pat. No. 5,516,956.

[21] Appl. No.: 557,251

[22] Filed: Nov. 14, 1995

Related U.S. Application Data

[63] Continuation-in-part of Ser. No. 342,322, Nov. 18, 1994, Pat. No. 5,516,956, and Ser. No. 469,602, Jun. 8, 1995, and Ser. No. 471,631, Jun. 6, 1995, Pat. No. 5,625,104.

[51] Int. Cl.⁶ ........................................................ C07C 5/22
[52] U.S. Cl. ........................... 585/481; 585/482; 585/486; 585/805
[58] Field of Search .................................... 585/475, 481, 585/482, 486, 313, 805

[56] References Cited

U.S. PATENT DOCUMENTS

| | | | |
|---|---|---|---|
| Re. 31,782 | 12/1984 | Olson et al. | 585/481 |
| 4,090,981 | 5/1978 | Rodewald | 252/455 |
| 4,117,026 | 9/1978 | Haag et al. | 260/671 |
| 4,163,028 | 7/1979 | Tabak et al. | 585/481 |
| 4,312,790 | 1/1982 | Butter et al. | 252/455 Z |
| 4,477,583 | 10/1984 | Rodewald | 502/71 |
| 4,582,815 | 4/1986 | Bowes | 502/64 |
| 4,783,568 | 11/1988 | Schmidt | 585/477 |
| 4,899,011 | 2/1990 | Chu et al. | 585/481 |
| 4,950,835 | 8/1990 | Wang et al. | 585/467 |
| 5,349,114 | 9/1994 | Lago et al. | 585/475 |
| 5,365,003 | 11/1994 | Chang et al. | 585/470 |
| 5,365,004 | 11/1994 | Beck et al. | 585/475 |
| 5,367,099 | 11/1994 | Beck et al. | 585/475 |
| 5,371,312 | 12/1994 | Lago et al. | 585/475 |
| 5,382,737 | 1/1995 | Beck et al. | 585/475 |
| 5,516,956 | 5/1996 | Abichandani et al. | 585/481 |

*Primary Examiner*—Shrive Beck
*Assistant Examiner*—Timothy Meeks
*Attorney, Agent, or Firm*—Malcolm D. Keen; Blossom E. Loo

[57] ABSTRACT

A mixture of aromatic hydrocarbons, comprising ethylbenzene and at least one xylene, is treated to convert the ethylbenzene to compounds that may be removed from the aromatic hydrocarbon stream and to isomerize any xylenes present. The ethylbenzene conversion catalyst is one that is effective for ethylbenzene conversion with minimal xylene loss, e.g., a silica bound intermediate pore size zeolite that has been selectivated. The xylene isomerization catalyst is one which is effective to catalyze xylene isomerization. Each of the catalysts of this invention may contain one or more hydrogenation or dehydrogenation components.

42 Claims, No Drawings

SELECTIVE ETHYLBENZENE CONVERSION

CROSS REFERENCE TO RELATED APPLICATIONS

This is a continuation-in-part of U.S. application Ser. No. 08/342,322, filed Nov. 18, 1994, now U.S. Pat. No. 5,516,956; U.S. application Ser. No. 08/469,602, filed Jun. 6, 1995; and U.S. application Ser. No. 08/471,631, filed Jun. 6, 1995, now U.S. Pat. No. 5,625,104, each incorporated by reference.

FIELD OF THE INVENTION

This invention is directed to a process for ethylbenzene conversion. This process uses a selectivated catalyst, optionally containing a hydrogenation-dehydrogenation function, to produce high ethylbenzene conversion levels, while at the same time producing low xylene loss levels. This catalyst may be used in combination with a second catalyst to effect isomerization of xylenes present in the ethylbenzene depleted stream produced by the ethylbenzene conversion catalyst.

BACKGROUND

Para-xylene is a valuable chemical feedstock which may be separated for use in the synthesis of polyesters from mixed xylenes by fractional crystallization, among other methods. Benzene is a highly valuable product for use as a chemical raw material. Toluene is also a valuable product for use as a solvent, in chemical manufacturing processes, and as a high octane gasoline component.

Para-xylene may be derived from mixtures of $C_8$ aromatics separated from such raw materials as petroleum naphthas, particularly reformates, usually by selective solvent extraction. Principal sources of the mixtures of $C_8$ aromatics are catalytically reformed naphthas and pyrolysis gasolines or distillates. The $C_8$ aromatic fractions from these sources vary quite widely in composition but will usually be in the range of 10 to 32 wt. % ethylbenzene (EB) with the balance, xylenes, being divided approximately 50 wt. % meta and 25 wt. % each of para and ortho. The $C_8$ aromatics in such mixtures and their properties are:

|  | Freezing Point °F. | Boiling Point °F. | Density Lbs./U.S. Gal. |
|---|---|---|---|
| Ethylbenzene | −139.0 | 277.1 | 7.26 |
| Para-xylene | 55.8 | 281.3 | 7.21 |
| Meta-xylene | −53.3 | 281.8 | 7.23 |
| Ortho-xylene | −13.8 | 291.2 | 7.37 |

Calculated thermodynamic equilibria for the $C_8$ aromatic isomers at 850° F. are:

| Wt. % Ethylbenzene | 8.5 |
|---|---|
| Wt. % Para-xylene | 22.5 |
| Wt. % Meta-xylene | 48.0 |
| Wt. % Ortho-xylene | 21.5 |
| TOTAL | 100.0 |

Individual isomer products may be separated from the naturally occurring mixtures by appropriate physical methods. Ethylbenzene may be separated by fractional distillation, although this is a costly operation. Ortho-xylene may be separated by fractional distillation, and it is so produced commercially. Para-xylene may be separated from the mixed isomers by fractional crystallization, selective adsorption (e.g., the Parex process), or membrane separation.

As commercial use of para-xylene and ortho-xylene has increased, isomerization of the other $C_8$ aromatics to produce an equilibrium mixture of xylenes, and thus increase the yields of the desired xylenes, has become increasingly important.

Catalysts of zeolite, plus a metal, such as platinum, are of the type known as "dual functional catalysts" characterized by the provision of catalyst sites of different functions, each of which separately performs its function, often one step for each type of site in a multi-step reaction sequence. For example, acidic sites in a catalyst may be suitable for reactions such as ethylbenzene conversion and the metal may be suitable for reactions such as the hydrogenation of ethylene to ethane. Such catalysts and the sequential reaction sites are discussed and explained by P. B. Weisz, "Polyfunctional Heterogeneous Catalysis," Advances in Catalysis, 13, pp 137–190 (1962). Weisz describes some experiments in which the two types of sites are provided by separate entities, such as physical mixtures of particles each of which provides only one type of catalytic site. Isomerization of certain paraffins over physical mixtures of acidic silica-alumina and platinum on a carrier is specifically described.

In many processes for xylene isomerization, conversion of ethylbenzene is constrained by the need to hold conversion of xylenes to other compounds to acceptable levels. Thus, operating conditions are still selected to balance the disadvantages of xylene loss by transalkylation with the conversion of ethylbenzene.

Separation or removal of ethylbenzene from mixed xylene streams is frequently difficult and expensive. It is desirable to achieve high conversion of ethylbenzene with low xylene loss. If ethylbenzene conversion may be achieved with little or no xylene loss, then virtually all of the xylenes may be converted to para-xylene and potentially recovered (using a recycle of unconverted xylenes and a high efficiency para-xylene extraction process).

SUMMARY

The process of this invention is directed to converting high percentages of the ethylbenzene present in mixed ethylbenzene-xylene containing feeds while minimizing xylene loss and, optionally, converting xylenes to approximately the thermal equilibrium concentration. In this way, the volume of any recycle stream, complexity of the separation processes, and total xylene losses associated with the xylene recovery process may be minimized.

One mode of ethylbenzene (EB) reduction is generally through disproportionation to benzene (BZ) and diethylbenzene (DEB). A representation of this reaction is given below:

EB+EB→BZ+DEB          (1)

Another reaction for EB reduction is through dealkylation to BZ and ethylene (ETH). A representation of this reaction is given below:

EB→BZ+ETH          (2)

The ethylene produced is saturated to ethane using hydrogen in the presence of a hydrogenation catalyst, such as platinum. Several undesirable side reactions may also take place, leading to xylene (XYL) loss. Representations for some of the major side reactions are given below:

$$EB + XYL \rightarrow BZ + DMEB \qquad (3)$$

$$EB + XYL \rightarrow TOL + MEB \qquad (4)$$

$$XYL + XYL \rightarrow TOL + TMB \qquad (5)$$

$$ETH + XYL \rightarrow DMEB \qquad (6)$$

where:

DMEB is dimethylethylbenzene

TOL is toluene

MEB is methylethylbenzene and

TMB is trimethylbenzene.

In the process of this invention, any reaction leading to ethylbenzene destruction or conversion is referred to herein as "ethylbenzene conversion." Of these reactions, reactions as depicted by equations 1 and 2 are desirable. Reactions as depicted in equations 3 through 6 along with similar and related types of reactions are undesirable and are collectively referred to as reactions leading to xylene loss. Ethylbenzene conversion and xylene loss, as referred to herein, may be determined by comparing the amount of ethylbenzene and total xylenes in the product with the amount of these compounds in the feed. In addition to the above described reactions, the xylene isomerization reactions may occur simultaneously.

The present process comprises contacting an isomerization feed containing C$_8$ aromatics, such as ethylbenzene and xylenes, under conversion conditions sufficient to convert ethylbenzene present in the feed, while, at the same time, minimizing xylene loss, using an ethylbenzene conversion catalyst, and sufficient to isomerize xylenes to approximately the equilibrium concentration using a xylene isomerization catalyst.

Examples of conversion conditions include a temperature of from about 400° F. to about 1,000° F., a pressure of from about 0 to about 1,000 psig, a weight hourly space velocity (WHSV) of between about 0.1 and about 200 hr$^{-1}$, and a hydrogen, H$_2$, to hydrocarbon, HC, molar ratio of between 0.1 and about 10. The conversion conditions may include a temperature of from about 650° F. and about 900° F., a pressure of from about 10 and about 400 psig, a WHSV of between about 3 and about 50 hr$^{-1}$ and a H$_2$ to HC molar ratio of between about 0.2 and about 5.

This invention comprises a catalyst that is selective for ethylbenzene conversion while minimizing xylene loss when operated under suitable conversion conditions. In addition to the ethylbenzene conversion catalyst, other catalysts may also be used, such as one suitable to effect isomerization of xylenes in the ethylbenzene depleted stream to the extent that the amount of para-xylene in the isomerization product is approximately equal to or greater than that at the thermal equilibrium of the xylene(s) while, at the same time, minimizing xylene transalkylation and other reactions leading to xylene loss when operated under suitable conditions.

An embodiment of the present invention is a process for isomerizing xylenes in a feed containing ethylbenzene and xylenes, wherein para-xylene is present in the feed in a concentration less than that at thermal equilibrium, the process comprising the steps of: (a) contacting the feed under ethylbenzene conversion conditions with a first bed of a first catalyst, wherein the first catalyst requires at least 1200 minutes to sorb ortho-xylene in an amount equal to 30% of the equilibrium sorption capacity for xylenes at 120° C. and at a xylene partial pressure of 4.5±0.8 mm of mercury; and (b) contacting the effluent from step (a) under xylene isomerization conditions with a second bed of a second catalyst comprising an intermediate pore size zeolite, wherein the second catalyst requires less than 50 minutes to sorb ortho-xylene in an amount equal to 30% of the equilibrium sorption capacity for xylenes at 120° C. and at a xylene partial pressure of 4.5±0.8 mm of mercury.

The first catalyst mentioned above may comprise an intermediate pore size zeolite, e.g., ZSM-5, which has been selectivated either through the multiple impregnation, trim-selectivation, coke selectivation or combinations of these methods, as described herein. In particular, the first catalyst may be self-bound, may include a silica binder, and may include a binder that has no intentionally added alumina. Additionally, the first catalyst may require at least 3600, e.g., at least 10000 minutes, to sorb ortho-xylene in an amount equal to 30% of the equilibrium sorption capacity for xylenes at 120° C. and at a xylene partial pressure of 4.5±0.8 mm of mercury, e.g., if the first catalyst contains a zeolite component, the zeolite component of the first catalyst may have the stated ortho-xylene sorption times.

The second catalyst mentioned above may include any catalyst that promotes xylene isomerization. Examples of suitable catalysts include an intermediate pore size zeolite, e.g., ZSM-5, that optionally contains a hydrogenation or dehydrogenation component.

Another embodiment of the present invention is a process for aromatics production from a feed containing ethylbenzene and at least one xylene, the process comprising the steps of: (a) contacting the feed with a first catalyst under ethylbenzene conversion conditions to thereby produce an ethylbenzene depleted product, the first catalyst comprising a silica bound intermediate pore size zeolite having a crystal size between about 0.1 and 1μ that has been modified by being exposed to at least three selectivation sequences, each selectivation sequence comprising the steps of contacting the zeolite with a selectivating agent and subsequently calcining the selectivated zeolite, wherein the selectivating agent contains silicon; and (b) contacting the ethylbenzene depleted product with a second catalyst under xylene isomerization conditions.

DETAILED DESCRIPTION

Feedstock

In general, any aromatic C$_8$ mixture containing ethylbenzene and xylene may be used as feed to the process of this invention. Such mixture may have an ethylbenzene content in the approximate range of 5 to 60 weight percent, an ortho-xylene content in the approximate range of 0 to 35 weight percent, a meta-xylene content in the approximate range of 20 to 95 weight percent and a para-xylene range of 0 to 25 weight percent, e.g., may contain about 10 to 15 weight percent ethylbenzene with the balance xylenes. The feed in addition to the above aromatic C$_8$ mixture may contain non-aromatic hydrocarbons, i.e., naphthenes and paraffins in an amount up to 30 weight percent. The feed may also contain a small amount of materials, e.g., aromatics, heavier than C$_8$ aromatics. The invention provides means to process a mixture of C$_8$ aromatics such as that derived, after other known processing steps, such as solvent extraction and distillation, from catalytic reforming of a petroleum naphtha or the mixture derived from the disproportionation of toluene to mixed xylenes or the mixture derived from the highly selective conversion of toluene to para-xylene to a mixture of reduced ethylbenzene content and, optionally, to achieve increased recovery of para-xylene.

The present invention is especially suitable for the reduction of ethylbenzene content in $C_8$ aromatic streams that contain about 2 to 60 wt. % ethylbenzene, e.g., about 5 to 50 wt. % ethylbenzene. This range is intended to span the range of ethylbenzene concentrations of streams that are derived from a reformer and a pyrolysis gasoline unit. The present catalyst may have high activity for cracking of normal and branched paraffins of the type present in unextracted $C_8$ aromatic streams.

Process Conditions

In accordance with the present invention, the above described feedstock may be contacted with the catalyst system under suitable conversion conditions to effect ethylbenzene conversion and to effect xylene isomerization. Examples of these conversion conditions include a temperature of from about 400° F. to about 1,000° F., a pressure of from about 0 to about 1,000 psig, a weight hourly space velocity (WHSV) of between about 0.1 and about 200 $hr^{-1}$, and a hydrogen, $H_2$, to hydrocarbon, HC, molar ratio of between about 0.1 and about 10. Alternatively, the conversion conditions may include a temperature of from about 650° F. and about 900° F., a pressure of from about 50 and about 400 psig, a WHSV of between about 3 and about 50 $hr^{-1}$ and a $H_2$ to HC molar ratio of between about 0.5 and about 5. The WHSV is based on the weight of catalyst composition, i.e., the total weight of active catalyst plus, if used, binder therefor.

One function of the present invention is to effect ethylbenzene conversion with minimal xylene loss. The ethylbenzene conversion products tend to be compounds that are more easily recovered or are more easily separated from the mixed xylenes than ethylbenzene itself. Optimally, the component effective for ethylbenzene conversion may be distinguished by limited capability for xylene isomerization. This limited capability for xylene isomerization arises from a feature of the present catalyst, a diffusion resistance for xylenes, particularly ortho-xylene and meta-xylene.

To effect high levels of conversion of ethylbenzene without excessive loss of xylenes to heavier aromatics and other components, the $C_8$ feed should be contacted with the catalyst of this invention, under suitable conversion conditions. After the ethylbenzene conversion reaction, the $C_8$ stream may be contacted under suitable conversion conditions with a catalyst that is suitable for isomerizing the xylene components of the $C_8$ feed. The conversion process described herein may be carried out as a batch type, semi-continuous or continuous operation. After use in a moving or fluidized bed reactor, the catalyst can be regenerated, in a regeneration zone in which the coke is burned from the catalyst in an oxygen containing atmosphere, e.g., air, at an elevated temperature after which the regenerated catalyst is recycled to the conversion zone for further contact with the charge stock. In a fixed bed reactor, regeneration can be carried out in a conventional manner by using initially an inert gas containing a small amount of oxygen (0.5 to 10 volume percent) to burn coke in a controlled manner so as to limit the temperature to a maximum of around about 450° C. to about 550° C.

In general, the xylene isomerization reaction is carried out in a fixed bed reactor containing the catalyst system described above. In one embodiment, the two components of the catalyst system are in sequential beds. That is, the catalyst which is effective for ethylbenzene conversion forms a first bed, while the other catalyst, which is effective for xylene isomerization, forms a second bed. The conversion process of the invention could be carried out in two different reactors, possibly even at different process conditions, such as temperatures. For example, the ethylbenzene conversion reaction could be carried out at a higher temperature than the xylene isomerization reaction. Further, when two different reactors are used, benzene, paraxylene, or other aromatics, could be removed between the reactors, thus further reducing the amount of xylene loss due to transalkylation or other reactions in the xylene isomerization reactor. An additional alternative would be where the ethylbenzene conversion reactor is located outside the xylene recovery and isomerization loop. The feed may be cascaded over the catalyst system disposed in sequential beds. In cascading, the feed is contacted with the two components of the catalyst system without intervening separation of light gases or materials such as benzene.

In embodiments below, the component of the catalyst system effective for ethylbenzene conversion is upstream with respect to the catalyst component which is effective to isomerize the xylene components of the $C_8$ aromatic feed. In this embodiment, the catalyst component which is effective for ethylbenzene conversion is employed in a volume sufficient to achieve the desired level of ethylbenzene conversion, generally a volume greater than 10 percent, e.g., greater than 25 percent, e.g., greater than 50 percent, e.g., greater than 55 percent, e.g., greater than 60 percent, e.g., greater than 75 percent, e.g., greater than 80 percent of the total catalyst volume.

After the conversion process, the product can be treated to isolate para-xylene and/or other desirable compounds. Thus, for example, the product could be fed to a variety of para-xylene recovery units, such as a crystalizer, a membrane separation unit, or a selective adsorption unit, and thus the para-xylene may be isolated and recovered. The residual product can be stripped of products lighter than $C_8$. Products heavier than $C_8$ in the residual product can be further processed or may be fractionated out. $C_8$ fractions from which para-xylene has been removed can be recycled to the isomerizer, e.g., fractions containing less than the equilibrium amount of para-xylene, e.g., less than about 2 weight percent para-xylene.

A result of the process of this invention is the conversion of 15% to 90% or more of the ethylbenzene contained in the mixed xylene feed to benzene and other components that are relatively easily removed from the mixed xylene stream. For example, ethylbenzene conversion levels of greater than about 30% are easily accomplished, e.g., greater than about 60%, e.g., greater than about 70%, e.g., greater than about 75%, e.g., greater than about 80%, e.g., greater than about 85%, e.g. 90% or more by weight. The high conversion of ethylbenzene using the selective catalyst and conversion conditions of the present invention results in a molar ratio of benzene produced to ethylbenzene consumed of greater than 0.5, e.g., greater than 0.65, e.g., greater than 0.75, e.g., greater than 0.8. Due to the unique properties of the catalyst and conversion conditions used as a part of this invention, this ethylbenzene conversion may be accomplished with little xylene loss, such as less than about 1% to 3%, for example xylene loss levels of less than about 3% are easily achieved, e.g., xylene loss levels of less than about 2%, e.g., xylene loss levels of less than about 1% may also be achieved.

Catalyst System

Catalysts useful in this invention may comprise an intermediate pore size zeolite having a Constraint Index within the approximate range of 1 to 12 (e.g., zeolites having less than about 7 Angstroms pore size, such as from about 5 to less than about 7 Angstroms) having a silica to alumina molar ratio of at least about 5, e.g., at least about 12, e.g., at least 20.

The silica to alumina ratio referred to may be determined by conventional analysis. This ratio is meant to represent, as closely as possible, the molar ratio in the rigid anionic framework of the zeolite crystal and to exclude silicon and aluminum in the binder or in cationic or other form within the channels.

Examples of intermediate pore size zeolites useful in this invention include ZSM-5 (U.S. Pat. Nos. 3,702,886 and Re. 29,948); ZSM-11 (U.S. Pat. No. 3,709,979); ZSM-12 (U.S. Pat. No. 3,832,449); ZSM-22 (U.S. Pat. No. 4,556,477); ZSM-23 (U.S. Pat. No. 4,076,842); ZSM-35 (U.S. Pat. No. 4,016,245); ZSM-48 (U.S. Pat. No. 4,397,827); ZSM-57 (U.S. Pat. No. 4,046,685); and ZSM-58 (U.S. Pat. No. 4,417,780). The entire contents of the above references are incorporated by reference herein.

A characteristic of the crystal structure of some of the zeolites useful in this invention is that it provides constrained access to and egress from the intracrystalline free space by virtue of having an effective pore size intermediate between the small pore Linde A and the large pore Linde X, i.e. the pore windows of the structure have a size such as would be provided by 10-membered rings of oxygen atoms. It is to be understood, of course, that these rings are those formed by the regular arrangement of the tetrahedra making up the anionic framework of the crystalline aluminosilicate, the oxygen atoms themselves being bonded to the silicon or aluminum atoms at the centers of the tetrahedra.

The intermediate pore size zeolites referred to herein have an effective pore size such as to freely sorb materials such as normal hexane, toluene, para-xylene, and ethylbenzene. In addition, the structure must provide constrained access to larger molecules. It is sometimes possible to judge from a known crystal structure whether such constrained access exists. For example, if the only pore windows in a crystal are formed by 8-membered rings of oxygen atoms, then access to molecules of larger cross-section than normal hexane is excluded and the zeolite is not an intermediate pore size zeolite. Windows of 10-membered rings are preferred, although in some instances excessive puckering of the rings or pore blockage may render these zeolites ineffective.

The Constraint Index referred to above also qualifies the zeolite useful in this invention as having an intermediate pore size, as will be more fully described below.

Rather than attempt to judge from crystal structure whether or not a zeolite possesses the necessary access to molecules larger than normal paraffins, a simple determination of the Constraint Index may be made. The method by which Constraint Index is determined is described fully in U.S. Pat. No. 4,016,218, incorporated herein by reference for details of the method. Constraint Index (CI) values for some typical zeolites including some which are suitable as catalysts in the process of this invention are as follows:

|  | CI (at test temperature) |  |
|---|---|---|
| ZSM-4 | 0.5 | (316° C.) |
| ZSM-5 | 6–8.3 | (371° C.–316° C.) |
| ZSM-11 | 5–8.7 | (371° C.–316° C.) |
| ZSM-12 | 2.3 | (316° C.) |
| ZSM-20 | 0.5 | (371° C.) |

-continued

|  | CI (at test temperature) |  |
|---|---|---|
| ZSM-22 | 7.3 | (427° C.) |
| ZSM-23 | 9.1 | (427° C.) |
| ZSM-34 | 50 | (371° C.) |
| ZSM-35 | 4.5 | (454° C.) |
| ZSM-48 | 3.5 | (538° C.) |
| ZSM-50 | 2.1 | (427° C.) |
| MCM-22 | 0.6–1.5 | (399° C.–454° C.) |
| TMA Offretite | 3.7 | (316° C.) |
| TEA Mordenite | 0.4 | (316° C.) |
| Clinoptilolite | 3.4 | (510° C.) |
| Mordenite | 0.5 | (316° C.) |
| REY | 0.4 | (316° C.) |
| Amorphous Silica-alumina | 0.6 | (538° C.) |
| Dealuminized Y | 0.5 | (510° C.) |
| Erionite | 38 | (316° C.) |
| Zeolite Beta | 0.6–2.0 | (316° C.–399° C.) |

The above-described Constraint Index provides a definition of those zeolites which may be useful in the process of the present invention. The very nature of this parameter and the above-referenced procedure by which it is determined, however, admits of the possibility that a given zeolite can be tested under somewhat different conditions and thereby exhibit different Constraint Indices. Constraint Index appears to vary somewhat with the severity of the conversion operation and the presence or absence of binder material. Similarly, other variables such as crystal size of the zeolite, the presence of occluded contaminants, etc., may affect the observed Constraint Index value. It will therefore be appreciated that it may be possible to select test conditions, e.g., temperature, as to establish more than one value for the Constraint Index of a particular zeolite. This explains the range of Constraint Indices for some zeolites, such as ZSM-5, ZSM-11, MCM-22, and Beta.

The zeolite, either directly or via initial ammonium exchange followed by calcination, may be hydrogen exchanged such that a predominant proportion of its exchangeable cations are hydrogen ions. It is contemplated that more than 50 percent and preferably more than 75 percent of the cationic sites of the crystalline aluminosilicate zeolite will be occupied by hydrogen ions. ZSM-5 in the hydrogen exchanged form may be referred to herein as HZSM-5.

Original ions, e.g., alkali or alkaline earth metal, of the as-synthesized zeolite can be replaced in accordance with techniques well known in the art, at least in part, by ion exchange with other ions. Typical ion exchange techniques would be to contact the synthetic zeolite with a solution containing a salt of the desired replacing ion or ions. Examples of such salts include the halides, e.g., chlorides, nitrates and sulfates. Representative ion exchange techniques are disclosed in a wide variety of patents including U.S. Pat. Nos. 3,140,249; 3,140,251; and 3,140,253, each incorporated by reference herein.

As indicated above, the catalyst is a zeolite which may be associated with a hydrogenation-dehydrogenation component. Examples of such components include the oxide, hydroxide, sulfide, or free metal (i.e., zero valent) forms of Group VIIIA metals (i.e., Pt, Pd, Ir, Rh, Os, Ru, Ni, Co, and Fe), Group VIIA metals (i.e., Mn, Tc, and Re), Group VIA metals (i.e., Cr, Mo, and W), Group VB metals (i.e., Sb and Bi), Group IVB metals (i.e., Sn and Pb), Group IIIB metals (i.e., Ga and In), and Group IB metals (i.e., Cu, Ag and Au). Noble metals (i.e., Pt, Pd, Ir, Rh, Os and Ru) are preferred hydrogenation/dehydrogenation components. Combinations of catalytic forms of such noble or non-noble metal, such as combinations of Pt with Sn, may be used. The metal may be in a reduced valence state, e.g., when this component is in the form of an oxide or hydroxide. The reduced valence state of this metal may be attained, in situ, during the course of a reaction, when a reducing agent, such as hydrogen, is included in the feed to the reaction.

The hydrogenation/dehydrogenation component may be incorporated into the catalyst by methods known in the art, such as ion exchange, impregnation or physical admixture. For example, solutions of appropriate metal salts may be contacted with the remaining catalyst components, either before or after selectivation of the catalyst, under conditions sufficient to combine the respective components. The metal containing salt may be water soluble. Examples of such salts include chloroplatinic acid, tetrammineplatinum complexes, platinum chloride, tin sulfate and tin chloride. The metal may be incorporated in the form of a cationic, anionic or neutral complex such as $Pt(NH_3)_4^{2+}$ and cationic complexes of this type will be found convenient for exchanging metals onto the zeolite. For example, a platinum modified catalyst can be prepared by first adding the catalyst to a solution of ammonium nitrate in order to convert the catalyst to the ammonium form. The catalyst is subsequently contacted with an aqueous solution of tetraamine platinum(II) nitrate or tetraamine platinum(II) chloride. Anionic complexes such as the vanadate or metatungstate ions are also useful for impregnating metals into the zeolites. Incorporation may be undertaken in accordance with the invention of U.S. Pat. No. 4,312,790, incorporated by reference herein. After incorporation of the metal, the catalyst can then be filtered, washed with water and calcined at temperatures of from about 250° C. to about 500° C.

The amount of hydrogenation/dehydrogenation component may be that amount which imparts or increases the catalytic ability of the overall catalyst to catalytically hydrogenate or dehydrogenate an organic compound under sufficient hydrogenation or dehydrogenation conditions, e.g., hydrogenate ethylene to ethane. This amount is referred to herein as a catalytic amount. The amount of the hydrogenation-dehydrogenation component may be from about 0.001 to about 10 percent by weight, e.g., from about 0.05 to about 5 percent by weight, e.g, from about 0.1 to about 2 percent by weight, although this will, of course, vary with the nature of the component, less of the highly active noble metals, particularly platinum, being required than of the less active base metals.

In practicing the process of the invention, the catalyst may be self-bound or it may be desirable to formulate the catalyst of the invention with another material resistant to the temperature and other conditions of the process. Such matrix materials include synthetic or naturally occurring substances as well as inorganic materials such as clay, silica, and/or metal oxides, such as zirconia, ceria, titania, and thoria. The preferred binder or support for the ethylbenzene conversion component is silica. Without intending to be bound thereby, it is believed that alumina binder catalyzed xylene isomerization reactions are further reduced through the use of inert silica binding for the ethylbenzene conversion catalyst. Also, the binder for the ethylbenzene conversion component may contain no intentionally added alumina. The metal oxides may be naturally occurring or in the form of gelatinous precipitates or gels including mixtures of silica and metal oxides. Naturally occurring clays which can be composited with the zeolite include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-berylia, silica-titania, as well as ternary compounds such as silica-alumina-thoria, silica-alumina-zirconia, silica-alumina-magnesia, and silica-magnesia-zirconia. A mixture of these components could also be used. The matrix may be in the form of a cogel. The relative proportions of zeolite component and inorganic oxide gel matrix on an anhydrous basis may vary widely with the zeolite content ranging from between about 1 to about 99 percent by weight and more usually in the range of about 10 to about 80 percent by weight of the dry composite, e.g., about 65% zeolite with about 35% binder.

The form and the particle size of the catalyst may vary depending, for example, on the type of reaction system employed. Non-limiting examples of the shapes of the catalyst which may be independently employed for either or both of the catalysts in the present invention include balls, pebbles, spheres, cylinders, extrudates, channeled monoliths, honeycombed monoliths, microspheres, pellets or structural shapes, such as lobes, trilobes, quadralobes, pills, cakes, honeycombs, powders, granules, and the like, formed using conventional methods, such as extrusion or spray drying. Where, for example, the final particles are designed for use as a fixed bed, the particles may preferably be formed into particles having a minimum dimension of at least about 0.01 inch and a maximum dimension of up to about one-half inch or one inch or more. Spherical particles having a diameter of about 0.03 inch to about 0.25 inch, preferably about 0.03 inch to about 0.15 inch, are often useful, especially in fixed bed or moving bed operations. With regard to fluidized bed systems, the major amount by weight of the particles may have a diameter in the range of about 10 microns to about 250 microns, e.g., about 20 microns to about 150 microns.

The zeolite component of catalysts suitable for use in the present invention may be characterized by different xylene diffusion properties or xylene sorption capabilities. In particular, it has been found that the ethylbenzene conversion catalyst should possess an equilibrium sorption capacity of xylene, which can be either para, meta, ortho or a mixture thereof, frequently para-xylene, since this isomer reaches equilibrium within the shortest time, of at least 1 gram per 100 grams of zeolite measured at 120° C. and a xylene pressure of 4.5±0.8 mm of mercury and an ortho-xylene sorption time for 30 percent of the xylene sorption capacity of greater than 1200 minutes (at the same conditions of temperature and pressure) are required in order to achieve the desired level of ethylbenzene conversion while maintaining the desired level of xylene loss. The sorption measurements may be carried out gravimetrically in a thermal balance. The sorption test is described in U.S. Pat. Nos. 4,117,026; 4,159,282; 5,173,461; and Re. 31,782; each of which is incorporated by reference herein.

It has been found that zeolites exhibiting very high selectivity for ethylbenzene conversion while minimizing xylene loss require a very long time, up to and exceeding 1200 minutes to sorb ortho-xylene in an amount of 30% of total xylene sorption capacity. For those materials, it may be more convenient to determine the sorption time for a lower extent of sorption, such as 5%, 10%, or 20% of capacity, and then to estimate the 30% sorption time by applying the following multiplication factor, F, as illustrated for 5% sorption:

$$t_{0.3} = F \cdot t_{0.05}$$

| Percent of sorption capacity | Factor, F, to estimate 30% sorption time, $t_{0.3}$ |
|---|---|
| 5 | 36 |
| 10 | 9 |
| 20 | 2.25 |

Alternatively, $t_{0.3}$ may be calculated for other sorption times at less than 30% of xylene capacity using the following relationship:

$$t_{0.3} = \left(\frac{0.3}{0.x}\right)^2 (t_{0.x})$$

where $t_{0.3}$—sorption time for 30% of total xylene capacity $t_{0.x}$—sorption time for x% of total xylene capacity 0.x—fractional amount of ortho-xylene sorption to total xylene capacity In accordance with the invention, the zeolite component of the catalyst that is effective for ethylbenzene conversion may have a $t_{0.3}$ value (in minutes) for ortho-xylene in excess of about 1200, e.g., greater than about 1500, e.g., greater than about 2000 minutes, e.g., greater than about 2500 minutes, e.g., greater than about 3000 minutes, e.g., greater than about 3600 minutes, e.g., greater than 10000 minutes, e.g., about 14760 minutes or greater. Contrast this with the zeolite component of the catalyst that is suitable for xylene isomerization, but need not be selective for ethylbenzene conversion. The zeolite component of this catalyst may have a $t_{0.3}$ time for ortho-xylene of less than 50 minutes, e.g., less than about 20 minutes, e.g., less than about 10 minutes, e.g., about 1 minute or less.

Ethylbenzene Conversion Catalyst

The alpha value of the catalyst which is effective to convert ethylbenzene may be at least about 5. The alpha value of that component may range from about 75 to 5000 or more, and it may even range from about 100 to about 2000. The xylene diffusion properties of this component may be such that, under ethylbenzene conversion conditions, the catalyst is capable of only a limited amount of xylene isomerization. For example, the ethylbenzene conversion catalyst may be one that meets the following test: producing less than 12 weight percent para-xylene when contacting a feed containing 60 weight percent meta-xylene, 20 weight percent ortho-xylene, and 20 weight percent ethylbenzene at a temperature of 800° F. (426.7° C.), a pressure of 150 psig (1136 kPaa), a weight hourly space velocity (WHSV) of 20 hr$^{-1}$, and a hydrogen to hydrocarbon molar ratio of 1. In the above test, the ethylbenzene conversion catalyst may even produce smaller amounts of para-xylene, e.g., less than 10 weight percent para-xylene, e.g., less than 6 weight percent para-xylene, e.g., less than 3 weight percent, e.g., less than 1 weight percent para-xylene, while converting more than 15 weight percent, e.g., more than 30 weight percent or even more than 65 weight percent of the ethylbenzene and while producing less than 3 weight percent xylene loss, e.g. less than 1 weight percent xylene loss. Further, in the above test, the activity of this catalyst may be such that, under the conditions of this test, less than 10 weight percent $C_5^-$ material may be produced, e.g., less than 6 weight percent, e.g., less than 3.5 weight percent, e.g., less than 3 weight percent $C_5^-$ material.

As pointed out above, the parent (unselectivated) zeolite component of this catalyst may be one characterized by a Constraint Index within the approximate range of 1 to 12. This parameter embraces a number of zeolites, some of which are described above. When, as in an embodiment described below, the zeolite component is ZSM-5, the requisite diffusional properties may be provided by providing ZSM-5 in suitable crystal sizes as will be further described herein, which, optionally, have been further coated, as will be more fully described below, at least once, e.g., at least twice, e.g., three times or more, e.g., 4 to 6 times with a silicon selectivating agent described herein, wherein each coating of selectivating agent is applied to the zeolite by a process comprising the steps of contacting the zeolite with a liquid organosilicon selectivating agent present in a liquid carrier and subsequently calcining the catalyst in an oxygen containing atmosphere to thereby produce the desired diffusion properties in the catalyst. As mentioned above, the zeolite may be bound with silica before being coated, after being coated or between successive coatings. Suitable selectivating agents are those which inhibit the diffusivity of the zeolite, particularly the diffusivity of the zeolite to ortho-xylene and meta-xylene. Alternatively, the desired diffusional properties may be achieved through the use of trim-selectivation or coke selectivation, as further described herein, either alone, or in combination with one or more coatings of the selectivating agent described above.

ZSM-5 crystals may be divided by crystal size into at least 3 broad groups. These crystal sizes range from the small crystal size (e.g., about 0.02 to about 0.2µ, e.g., about 0.02 to about 0.05µ); medium crystal size (e.g., about 0.2 to about 1µ, e.g., about 0.2 to about 0.5µ); and large crystal size (e.g., greater than about 1µ, e.g., greater than about 2µ up to about 20µ). Recognizing that zeolite crystal size determination may be accomplished using a variety of methods, as will be further described below, a number of examples of methods to produce the various zeolite crystal sizes are listed. Crystals prepared by these methods may be used to define the different size groups. Examples of methods that may be used to prepare small crystal size ZSM-5 are given in U.S. Pat. Nos. 4,117,026 (Example 3); 4,526,879 (Examples 1, 2, 6, and 7); and 4,899,011 in Col. 9, lines 6–53. Examples of methods that may be used to prepare medium crystal size ZSM-5 are given in U.S. Pat. Nos. 3,702,886 (Examples 2 and 26); 4,175,114; 4,199,556; 4,341,748; 4,375,458 (Examples 4 and 5); 5,243,117; and Great Britain Patent No. 1,581,513 (Examples 1 and 4). Examples of methods that may be used to prepare large crystal size ZSM-5 include U.S. Pat. Nos. 3,702,886 (Example 27); 4,375,458 (all examples except 4, 5 and 16); 5,182,090 (Examples 1, 2, 14 through 24, and 26); and Great Britain Patent No. 1,581,513 (Examples 2 and 3). All of the above described patents are incorporated by reference herein.

The accurate direct measurement of the crystal size of zeolite materials is frequently very difficult. Microscopy methods, such as SEM and TEM, may be used, but these methods require measurements of a large number of crystals, and, for each crystal measured, values may be evaluated in up to three dimensions. Furthermore, in order to more completely characterize the crystal size of a batch of crystals, one should calculate the average crystal size as well as the degree of variance from this average in terms of a crystal size distribution.

If desired, rather than relying upon a complex evaluation of crystal size, crystal size may be expressed in terms of a calculated value of average crystal size obtained by measuring the rate of sorption of 2,2-dimethylbutane at 90° C. and 60 torr hydrocarbon pressure. The crystal size is computed by applying the diffusion equation given by J. Crank, *The Mathematics of Diffusion*, Clarendon Press, 52–56 (1957), for the rate of sorbate uptake by a solid whose diffusion properties can be approximated by a plane sheet model. In addition, the diffusion constant of 2,2-dimethylbutane, D, under these conditions, is taken to be $1.5 \times 10^{-14}$ cm$^2$/sec. The relation between crystal size measured in microns, d, and diffusion time measured in minutes, $t'_{0.3}$, the time required for the uptake of 30% capacity of hydrocarbon, is:

$$d=0.0704 \times t'_{0.3}{}^{1/2}$$

One example of a large crystal material has a sorption time, $t'_{0.3}$, of 497 minutes, which gives a calculated crystal size of 1.6 microns. A crystal having a sorption time of 7.8 minutes would have a calculated size of 0.20 microns.

If ZSM-5 is the zeolite used as the ethylbenzene conversion component of this invention, it may comprise a medium or large crystal size. If another intermediate pore size zeolite is used as the ethylbenzene conversion component, the crystal size may need to be adjusted from those given above for best performance.

Procedures for preparing silica bound ZSM-5 are described in U.S. Pat. Nos. 4,582,815; 5,053,374; and 5,182,242, incorporated by reference herein. A particular procedure for binding ZSM-5 with a silica binder involves an extrusion process.

A particular process for preparing silica bound ZSM-5 may comprise the steps of:

(a) mulling and then extruding a mixture comprising water, ZSM-5, colloidal silica and sodium ions under conditions sufficient to form an extrudate having an intermediate green strength sufficient to resist attrition during ion exchange step (b) set forth hereinafter;

(b) contacting the uncalcined extrudate of step (a) with an aqueous solution comprising ammonium cations under conditions sufficient to exchange cations in said ZSM-5 with ammonium cations; and (c) calcining the ammonium exchanged extrudate of step (b) under conditions sufficient to generate the hydrogen form of said ZSM-5 and increase the crush strength of said extrudate.

Another method of silica binding uses a suitable silicone resin, e.g., a high molecular weight, hydroxy functional silicone, such as Dow Corning Q6-2230 silicone resin in a method disclosed in U.S. Pat. No. 4,631,267, incorporated by reference herein. Other silicone resins that may be used in the method of this invention include those described in U.S. Pat. No. 3,090,691. When a silicone resin is used, a suitable polar, water soluble carrier, such as methanol, ethanol, isopropyl alcohol, N-methyl pyrrolidone or a dibasic ester may also be used along with water as needed. Dibasic esters that may be useful in this invention include dimethyl glutarate, dimethyl succinate, dimethyl adipate, and mixtures thereof, one example of which is DuPont Chemical Co. DBE, which typically comprises about 50 to 75 percent dimethyl glutarate, 10 to 25 percent dimethyl adipate, 19 to 26 percent dimethyl succinate and less than about 0.2 wt. % methanol.

Extrusion aids may also be useful in the preparation of the catalysts of this invention. Methyl cellulose is a suitable extrusion aid, and one particular methyl cellulose that is effective as an extrusion aid in the method of this invention is a hydroxypropyl methyl cellulose, such as K75M Methocel™, available from Dow Chemical Co. Methyl cellulose may also be used alone or in combination with other binder or matrix material as a burn-out material to increase the porosity of the catalysts.

Various methods are known in the art for increasing the selectivity of zeolite catalysts. One such method is to modify the catalyst by treatment with a "selectivating agent." For example, U.S. Pat. Nos. 5,173,461; 4,950,835; 4,927,979; 4,465,886; 4,477,583; 4,379,761; 4,145,315; 4,127,616; 4,100,215; 4,090,981; 4,060,568; and 3,698,157 disclose specific methods for contacting a catalyst with a selectivating agent containing silicon ("silicon compound"). Also, U.S. Pat. Nos. 5,367,099; 5,382,737; 5,365,004; 5,403,800; 5,406,015; and U.S. application Ser. No. 08/069,251 disclose methods for silicon selectivation of catalysts and use of those catalysts in toluene and ethylbenzene disproportionation. Each of the above patents and patent application are incorporated by reference herein.

Traditionally, ex situ pre-selectivation of zeolites has involved single applications of the modifying compound. It may be noted, however, that the suggestion of multiple treatments was made in U.S. Pat. No. 4,283,306 to Herkes. The Herkes patent discloses the promotion of crystalline silica catalyst by application of an amorphous silica such as ethylorthosilicate (i.e., tetraethylorthosilicate). The Herkes patent contrasts the performance of catalyst treated once with an ethylorthosilicate solution followed by calcination against the performance of catalyst treated twice with ethylorthosilicate and calcined after each treatment. The Herkes disclosure shows that the twice-treated catalyst is less active and less selective than the once-treated catalyst as measured by methylation of toluene by methanol, indicating that the multiple ex situ selectivation confers no benefit and in fact reduces a catalyst's efficacy in shape-selective reactions.

In accordance with one selectivation method, the multiple impregnation method, the catalyst is selectivated by one or more treatments with a liquid organosilicon compound in a liquid carrier, each treatment being followed by calcination of the treated material in an oxygen containing atmosphere, e.g., air. More particularly, for example, with reference to the above-mentioned steps (a)–(c), this first selectivation method may involve the additional steps of:

(d) contacting the calcined extrudate of step (c) with a liquid comprising a liquid carrier and at least one organosilicon selectivating agent having at least two silicon atoms per molecule under conditions sufficient to incorporate said organosilicon selectivating agent in the extrudate, (e) calcining the extrudate of step (d) under conditions sufficient to decompose said organosilicon selectivating agent and to remove any residue of said liquid carrier from said extrudate; and, optionally, (f) repeating selectivation steps (d) and (e) at least once.

Another method for selectivating the ethylbenzene conversion catalyst, trim-selectivation, involves passing a feed stream comprising hydrogen and an aromatic (e.g., toluene) or a paraffin (e.g., hexane or decane) and an organosilicon compound over HZSM-5, e.g. silica bound ZSM-5, under conditions sufficient to deposit a residue of organosilicon compound on the ZSM-5.

The above-mentioned first method for selectivating the zeolite, wherein the zeolite, e.g., HZSM-5, is treated by multiple impregnation treatments, is referred to herein as the multiple impregnation method. The above-mentioned second method for selectivating the zeolite, wherein the zeolite, e.g., HZSM-5, is treated under trim-selectivation conditions, is referred to herein as the trim-selectivation method. Another method for selectivating the zeolite, described herein, which includes decomposing an organic compound on and in the zeolite, is referred to herein as the coke selectivation method. The present catalyst may be selectivated by any of the above selectivation methods or by more than one selectivation method used in combination.

In accordance with the multiple impregnation method, the zeolite, e.g., HZSM-5, is treated at least once, e.g, at least twice, e.g., 3 times or more, e.g., from 4 to 6 times, with a liquid medium comprising a liquid carrier and at least one liquid organosilicon compound. The organosilicon compound may be present in the form of a solute dissolved in the liquid carrier or in the form of emulsified droplets in the liquid carrier. The liquid carrier may be water, an organic liquid or a combination of water and an organic liquid. Particularly when the liquid medium comprises an emulsion of the organosilicon compound in water, the liquid medium may also comprise an emulsifying agent, such as a surfactant. For the purposes of the present disclosure, it will be understood that a normally solid organosilicon compound will be considered to be a liquid (i.e., in the liquid state) when it is dissolved or emulsified in a liquid medium. The liquid carrier may be water, an organic liquid or a combination of water and an organic liquid. Particularly when the liquid medium comprises an emulsion of the organosilicon compound in water, the liquid medium may also comprise an emulsifying agent, such as a surfactant. As mentioned above, the zeolite may be silica bound before selectivation, after selectivation, or between successive selectivation coatings.

Various organic compounds have been employed as carriers for silicon compounds in the silicon impregnation methods applied to zeolite catalysts. For example, U.S. Pat. Nos. 4,145,315; 4,127,616; 4,090,981; and 4,060,568 describe the use of inter alia $C_{5-7}$ alkanes as solvents for silicon impregnation. When the catalyst is impregnated with an organosilicon compound included in an organic carrier, the organic carrier may be any organic compound or mixture of organic compounds which are capable of dissolving or otherwise suitably suspending the organosilicon compound. Such organic carriers may be hydrocarbons, such as linear, branched, and cyclic hydrocarbons having five or more, especially 7 or more, carbon atoms per molecule, e.g., alkanes, such as heptane, octane, nonane, decane, undecane and dodecane. The boiling point of the organic compound, e.g., alkane, may be greater than about 70° C. Mixtures of low volatility organic compounds, such as hydrocracker recycle oil, may be employed as carriers. Particularly preferred organic carriers are decane and dodecane.

The organosilicon compound which is used to selectivate the zeolite may be a silicone, siloxane or a silane. Silicones are defined herein as those compounds wherein silicon atoms are bonded to one another via oxygen atoms. Silanes are defined herein as those compounds wherein silicon atoms are bonded directly to one another. The organosilicon compound preselectivating agent may be, for example, a silicone, a siloxane, a silane or mixtures thereof. These organosilicon compounds may have at least 2 silicon atoms per molecule. These organosilicon compounds may be solids in pure form, provided that they are soluble or otherwise convertible to the liquid form upon combination with the liquid carrier medium. The molecular weight of the silicone, siloxane or silane compound employed as a preselectivating agent may be between about 80 and about 20,000, and preferably within the approximate range of 150 to 10,000.

The kinetic diameter of the selectivating agent may be larger than the zeolite pore diameter, in order to avoid entry of the selectivating agent into the zeolite pores and any concomitant reduction in the internal activity of the zeolite. When a silicon compound is used that is of a size small enough to enter the pores of the catalyst crystal, it may be desirable to use the sodium form of the zeolite rather than the hydrogen form.

The silicone compound which may be used to selectivate the present zeolite may be considered to be constructed of a siloxy backbone structure capped with terminal groups. This siloxy backbone structure may be a chain structure represented by the formula

where p is from 1 to 100, e.g., 1 to 25, e.g., 1 to 9. This siloxy backbone structure may also be a cyclic structure represented by the formula

where q is from 2 to 10. Branched chain structures and composite chain/cyclic structures are also possible for the siloxy backbone of the silicone selectivating agent.

The hydrocarbyl groups which cap the available bonds of the siloxy backbone may have from 1 to 10 carbon atoms. Examples of such hydrocarbyl groups are methyl and phenyl.

Examples of silicone compounds having a chain siloxy backbone structure include those of the formula

where $R_1$ and $R_6$ are independently hydrogen, methyl, or phenyl; $R_2$, $R_3$, $R_4$, and $R_5$ are independently methyl or phenyl; and m is from 1 to 100, e.g., from 1 to 25, e.g., from 1 to 10, e.g., from 1 to 4. Preferably, no more than one phenyl group is bonded to each silicon atom. Particular examples of such silicone compounds having a chain siloxy backbone structure include hexamethyldisiloxane, decamethyltetrasiloxane and diphenyltetramethyldisiloxane. Particular examples of silicone compounds having a cyclic siloxy backbone structure include octamethylcyclotetrasiloxane and decamethylcyclopentasiloxane. Particular examples of silicone compounds having a branched siloxy backbone structure are tris-(trimethylsiloxy)-phenylsilane and tris-(trimethylsiloxy)-silane.

The silane compounds, useful as selectivating agents according to the present method, may have structures corresponding to the above-mentioned silicone compounds, wherein the silicon atoms are bonded directly to one another instead of via oxygen atoms. Examples of silanes having a chain backbone structure include those of the formula

where $R_1$ and $R_6$ are independently hydrogen, methyl, or phenyl; $R_2$, $R_3$, $R_4$, and $R_5$ are independently methyl or phenyl; and m is from 1 to 100, e.g., from 1 to 25, e.g., from 1 to 10, e.g., from 1 to 4. An example of such a silane compound is hexamethyldisilane.

Representative preselectivation silicone compounds include dimethyl silicone, diethyl silicone, phenylmethyl silicone, methylhydrogen silicone, ethylhydrogen silicone, phenylhydrogen silicone, methylethyl silicone, phenylethylsilicone, diphenyl silicone, methyltrifluoropropyl silicone, ethyltrifluoropropyl silicone, polydimethyl silicone, tetrachlorophenylmethyl silicone, tetrachlorophenylethyl silicone, tetrachlorophenylhydrogen silicone, tetrachlorophenylphenyl silicone, methylvinyl silicone, and ethylvinyl silicone. The preselectivating silicone, siloxane or silane compound need not be linear, but may be cyclic, for example, hexamethyl cyclotrisiloxane, octamethyl cyclotetrasiloxane, hexaphenyl cyclotrisiloxane and octaphenyl cyclotetrasiloxane. Mixtures of these compounds may also be used as preselectivating agents, as may silicones with other functional groups.

Preferred organosilicon preselectivating agents, particularly when the preselectivating agent is dissolved in an organic carrier or emulsified in an aqueous carrier, include dimethylphenyl methyl polysiloxane (e.g., Dow-550) and phenylmethyl polysiloxane (e.g., Dow-710). Dow-550 and Dow-710 are available from Dow Chemical Co., Midland, Mich.

When the organosilicon preselectivating agent is present in the form of a water soluble compound in an aqueous solution, the organosilicon may be substituted with one or more hydrophilic functional groups or moieties, which serve to promote the overall water solubility of the organosilicon compound. These hydrophilic functional groups may include one or more organoamine groups, such as $-N(CH_3)_3$, $-N(C_2H_5)_3$ and $-N(C_3H_7)_3$. A preferred water soluble organosilicon preselectivating agent is an n-propylamine silane, available as Hydrosil 2627 from Huls America. Particular water soluble organosilicon compounds, which may be used for multiple impregnations of the present catalyst, are referred to as amino silane polymers in U.S. Pat. No. 5,371,312, incorporated by reference herein. As mentioned previously herein, aqueous emulsions of organosilicon compounds comprising surfactants may be used for the impregnation of the present catalyst. Stable aqueous emulsions of organosilicon compounds (e.g., silicone oil) are described in U.S. application Ser. No. 08/141,758, filed Oct. 27, 1993, incorporated by reference herein.

The present zeolite may be selectivated by more than one selectivation method. In particular, prior to use in the present process, the zeolite may be contacted with an organosilicon compound, followed by calcination in an oxygen containing atmosphere. Such a pretreatment of the zeolite may be referred to herein as a preselectivation treatment.

In accordance with an example of a preselectivation method, the catalyst is preselectivated by single or multiple treatments with a liquid organosilicon compound in a liquid carrier, each treatment being followed by calcination of the treated material in an oxygen containing atmosphere, e.g., air.

When the zeolite is preselectivated by a single or multiple impregnation technique, the zeolite is calcined after each impregnation to remove the carrier and to convert the liquid organosilicon compound to a solid residue material thereof. This solid residue material is referred to herein as a siliceous solid material, insofar as this material is believed to be a polymeric species having a high content of silicon atoms in the various structures thereof. However, this siliceous solid residue material may also comprise carbon atoms in the structure thereof, resulting from the residue of the organo portion of the organosilicon compound used to impregnate the catalyst.

Following each impregnation, the zeolite may be calcined at a rate of from about 0.2° C./minute to about 5° C./minute to a temperature greater than 200° C., but below the temperature at which the crystallinity of the zeolite is adversely affected. This calcination temperature may be below 700° C., e.g., within the approximate range of 350° C. to 550° C. The duration of calcination at the calcination temperature may be from 1 to 24 hours, e.g., from 2 to 6 hours.

The impregnated zeolite may be calcined in an inert or oxidizing atmosphere. An example of such an inert atmosphere is a nitrogen, i.e., $N_2$, atmosphere. An example of an oxidizing atmosphere is an oxygen containing atmosphere, such as air. Calcination may take place initially in an inert, e.g., $N_2$, atmosphere, followed by calcination in an oxygen containing atmosphere, such as air or a mixture of air and $N_2$. Calcination should be performed in an atmosphere substantially free of water vapor to avoid undesirable uncontrolled steaming of the zeolite. The zeolite may be calcined once or more than once following each impregnation. The various calcinations following each impregnation need not be identical, but may vary with respect to the temperature, the rate of temperature rise, the atmosphere and the duration of calcination.

The amount of siliceous residue material which is deposited on the zeolite or bound zeolite is dependent upon a number of factors including the temperatures of the impregnation and calcination steps, the concentration of the organosilicon compound in the carrying medium, the degree to which the catalyst has been dried prior to contact with the organosilicon compound, the atmosphere used in the calcination and the duration of the calcination. A suitable amount of silicon on the catalyst is greater than 9 weight percent, e.g., greater than 12 weight percent, exclusive of the silica present in the binder or in the zeolite itself.

After the impregnation/calcination sequence, the catalyst may be subjected to steaming conditions sufficient to increase or decrease the activity and/or selectivity of the catalyst, as desired. Such conditions are disclosed in U.S. Pat. No. 5,349,114, incorporated by reference herein. The steaming conditions may include a temperature of from about 100° C. to about 800° C., e.g., from about 175° C. to about 325° C., with from about 1% to about 100% steam, e.g., from about 50% to about 100% steam, at a pressure of from about 0.01 psia to about 5000 psia, e.g. from about 14 psia to about 50 psia, and for a duration of about 0.1 to about 200 hours, e.g., from about 0.5 to about 24 hours, e.g., from about 3 to about 6 hours. Excessive steaming or steaming under too severe conditions may be detrimental to the activity and selectivity of the catalyst.

The present catalyst may comprise at least 0.03 wt. %., e.g., at least 0.1 wt. %, of alkali metal or alkaline earth metal, e.g., an amount effective to achieve the desired activity/selectivity. Particular alkali metals include Li, Na, K, Rb, and Cs. Particular alkaline earth metals include Mg, Ca, Sr, and Ba. The alkali metal or alkaline earth metal may be added by contacting the catalyst, in particular, the zeolite component of the catalyst, either before or after selectivation, with an aqueous solution containing an alkali metal, ion of an alkali metal, alkaline earth metal, or ion of an alkaline earth metal, optionally washing off excess solution using water or another solvent, and then drying the treated catalyst. The present alkali metal or alkaline earth metal incorporation or ion exchange procedure may be used to decrease the activity of the catalyst. The activity may be adjusted on a small scale to fine-tune batches of the catalyst for a particular use or the activity may be adjusted on a major scale to convert the catalyst from one type to another, thereby providing a means to manufacture different catalysts for different uses. When only a small amount of alkali metal or alkaline earth metal ions are incorporated into the catalyst, e.g., in accordance with an effort to fine-tune the activity of the catalyst, the alpha value of the catalyst may be reduced by a small amount, e.g., by 10% or less. However, when a larger amount of alkali metal or alkaline earth metal ions are exchanged onto the catalyst, e.g., in an effort to produce a low activity catalyst, the alpha value of the catalyst may be reduced by a larger amount, e.g., by at least 50%, e.g., at least 90%.

Sources of lithium ions include lithium acetate, lithium acetylsalicylate, lithium carbonate, lithium chlorate, lithium perchlorate, lithium chloride, lithium bromide, lithium fluoride, lithium iodide, lithium iodate, lithium nitrite, lithium nitrate, lithium oxalate, lithium palmitate, lithium salicylate, lithium sulfate, lithium tartarate, lithium sulfide, lithium thiocyanate, lithium phosphate, lithium ammonium phosphate, lithium hydroxide, lithium cyanide, and lithium stearate.

Sources of sodium ions include sodium acetate, sodium barbital, sodium benzoate, sodium carbonate, sodium chloride, sodium chlorate, sodium bromide, sodium bromate, sodium perchlorate, sodium chlorite, sodium hypochlorite, sodium cinnamate, sodium citrate, sodium cyanate, sodium cyanide, sodium ethylacetoacetate, sodium hydride, sodium hydrogen fluoride, sodium formate, sodium glutamate, sodium iodide, sodium iodate, sodium periodate, sodium hydroxide, sodium lactate, sodium methoxide, sodium ethoxide, sodium nitrate, sodium nitrite, sodium oleate, sodium oxalate, sodium palmitate, sodium phenoxide, sodium carbonate, sodium bicarbonate, sodium propionate, sodium salicylate, sodium stearate, sodium succinate, sodium sulfate, sodium persulfate, sodium hydrogen sulfate, sodium hydrogen sulfide, sodium sulfide, sodium sulfite, sodium tartarate, sodium thiocyanate, sodium thiosulfate, and sodium ammonium tartarate.

Sources of potassium ions include potassium acetate, potassium acetyl salicylate, potassium bromide, potassium bromate, potassium chloride, potassium camphorate, potassium carbonate, potassium chloride, potassium chlorate, potassium perchlorate, potassium hypochlorite, potassium chloroiodate, potassium citrate, potassium cyanate, potassium cyanide, potassium ethylsulfate, potassium hydride, potassium fluoride, potassium hydroxide, potassium iodate, potassium iodide, potassium lactate, potassium laurate, potassium malate, potassium methylsulfate, potassium nitrate, potassium nitrite, potassium oleate, potassium oxalate, potassium picrate, potassium phthalate, potassium piperate, potassium sorbate, potassium stearate, potassium sulfate, potassium succinate, potassium pyrosulfate, potassium sulfide, potassium hydrogen sulfide, potassium sulfite, potassium tartarate, potassium thiocyanate, potassium dithionate, and potassium xanthate.

Sources of cesium ions include cesium acetate, cesium benzoate, cesium bromide, cesium bromate, decium carbonate, cesium hydrogen carbonate, cesium chloride, cesium chlorate, cesium perchlorate, cesium fluoride, cesium formate, cesium hydride, cesium hydroxide, cesium iodide, cesium iodate, cesium periodate, cesium nitrate, cesium nitrite, cesium oxalate, cesium oxide, cesium salicylate, cesium sulfate, cesium sulfide, cesium tartarate, and cesium hydrogen tartarate.

Sources of magnesium ions include magnesium acetate, magnesium nitrate, magnesium chloride, magnesium bromide, magnesium benzoate, magnesium proprionate, magnesium 2-ethylhexoate, magnesium carbonate, magnesium formate, magnesium oxylate, magnesium amide, magnesium bromide, magnesium hydride, magnesium lactate, magnesium laurate, magnesium oleate, magnesium palmitate, magnesium silicylate, magnesium stearate, and magnesium sulfide.

Sources of calcium ions include calcium acetate, calcium butyrate, calcium carbonate, calcium chloride, calcium bromide, calcium fluoride, calcium iodide, calcium chlorate, calcium citrate, calcium cinnamate, calcium laurate, calcium maleate, calcium nitrate, calcium nitrite, calcium oxide, calcium propionate, and calcium sulfide.

Sources of barium ions include barium acetate, barium bromide, barium chloride, barium fluoride, barium ioxide, barium butyrate, barium chlorate, barium perchlorate, barium cyanide, barium dithionate, barium formate, barium nitrate, barium nitrite, barium oxide, barium propionate, and barium sulfide.

Sources of strontium ions include strontium acetate, strontium bromide, strontium carbonate, strontium chloride, strontium fluoride, strontium iodide, strontium formate, strontium chlorate, strontium lactate, strontium nitrate, strontium nitrite, strontium oxide, strontium hyponitrite, strontium salicylate, strontium sulfide, and strontium dithionate.

In accordance with the trim-selectivation method described herein, the catalyst may be contacted with a feed stream typically comprising hydrogen and an aromatic compound (e.g., toluene) or a paraffinic compound (e.g., hexane or decane) with the organosilicon compound under suitable trim selectivation conditions. These conditions may include a temperature ranging from about 100° C. to about 600° C., e.g., from about 300° C. to about 500° C., a pressure ranging from about 0 to about 2000 psig, e.g., from about 15 to about 800 psig, a mole ratio of hydrogen to hydrocarbons (e.g., toluene) from about 0.1 to 20, e.g., from about 0.1 to 10, e.g., from about 1 to about 4, and a weight hourly space velocity (WHSV) from about 0.1 to about 100 $hr^{-1}$, e.g., from about 0.1 to about 10 $hr^{-1}$. Toluene may comprise about 50 wt. % to 100 wt. %, e.g., at least 80 wt. %, of the hydrocarbons in the feedstock. Other hydrocarbons, such as benzene, xylenes and trimethylbenzenes, may also be present in the trim-selectivation feedstock.

The presence of a sufficient amount of hydrogen in the trim-selectivation feedstock is helpful to prevent rapid aging of the catalyst during the selectivation process. However, even when hydrogen is used in optimal fashion to prevent aging during the selectivation process, a small amount of carbonaceous deposit may form on the catalyst. As a result of this carbonaceous deposit, an elemental analysis of the trim-selectivated catalyst may reveal a carbon content significantly greater than the carbon content of the fresh catalyst prepared by the multiple impregnation method described herein. More particularly, the trim-selectivated catalyst may contain at least 2 wt. %, e.g., at least 4 wt. %, of carbon by elemental analysis, whereas the catalyst prepared by the multiple impregnation method may contain less than 0.5 wt. % of carbon as measured by elemental analysis. These weight percentages are expressed in terms of the weight of the entire catalyst including the zeolite, binder and optional components, such as hydrogenation/ dehydrogenation components.

The present catalyst may also be subjected to controlled coking. This controlled coking procedure is also referred to herein as coke selectivation. This optional coke selectivation may involve contacting the catalyst with a thermally decomposable organic compound at an elevated temperature in excess of the decomposition temperature of said compound but below the temperature at which the crystallinity of the zeolite is adversely affected. This contact temperature may be, for example, less than about 650° C. The catalyst may be coked in a reactor or other vessel that is different than that used for the ethylbenzene conversion, followed by transport of the coked catalyst to the ethylbenzene conversion reactor. Performance of coke selectivated catalyst for ethylbenzene conversion is not significantly degraded by the handling associated with transporting the catalyst between the reactor used to coke selectivate the catalyst and the ethylbenzene conversion catalyst. Coke selectivation is described in U.S. Pat. Nos. 5,234,875; 4,581,215; 4,508,836; 4,358,395; 4,117,026; and 4,097,543, incorporated by reference.

Organic materials, which may be used for this coke selectivation process, encompass a wide variety of compounds including by way of example, hydrocarbons, such as paraffins, cycloparaffins, olefins, cycloolefins and aromatics; oxygen-containing organic compounds, such as alcohols, aldehydes, ethers, ketones and phenols; and heterocyclics, such as furans, thiophenes, pyrroles and pyridines. A hydrogen cofeed may be used to deter the excessive build-up of coke. Further details regarding coke selectivation techniques are provided in the U.S. Pat. No. 4,117,026, as well as in U.S. application Ser. No. 08/069,251, incorporated by reference herein. An organosilicon cofeed may be, optionally, included along with the organic material feed used for coke selectivation. This organosilicon material may be selected from the organosilicon compounds mentioned hereinabove for use in the selectivation of the catalyst.

While not wishing to be bound by any theory, it is possible that the selectivity of the present ethylbenzene conversion catalyst is obtained by producing changes in the diffusion properties of the zeolite that favor the desired reactions and inhibit undesired reactions.

Isomerization Catalyst

The ethylbenzene conversion catalyst may be followed by a suitable isomerization catalyst. A suitable isomerization catalyst is one that is effective to isomerize the xylenes of the feed containing $C_8$ aromatics under suitable conditions. The isomerization catalyst may also have minimal activity for xylene transalkylation or other reactions leading to xylene loss under the same reaction conditions. The zeolite component of this catalyst may comprise an intermediate pore size zeolite, e.g., one having a Constraint Index between 1 and 12, specifically ZSM-5. The acidity of the ZSM-5 of this catalyst, expressed as the alpha value, may be less than about 150, e.g., less than about 100, e.g., at most 50, e.g., the alpha value may range from about 5 to about 25. Small crystal size zeolites, as defined herein, may be used in this catalyst.

When alpha value is examined, it is noted that the alpha value is an approximate indication of the catalytic cracking activity of the catalyst compared to a standard catalyst and it gives the relative rate constant (rate of normal hexane conversion per volume of catalyst per unit time). It is based on the activity of silica-alumina cracking catalyst taken as an alpha of 1 (rate constant is 0.016 $sec^{-1}$). The alpha test is described in U.S. Pat. No. 3,354,078; in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395. The higher alpha values correspond with a more active cracking catalyst.

EXAMPLE 1

A medium crystal ZSM-5 that was bound with silica, 65% zeolite and 35% silica, was tested to determine the time required to sorb ortho-xylene in an amount equal to 30% of the total xylene sorption capacity at 120° C. and 4.5±0.8 mm mercury, $t_{0.3}$. This catalyst will be referred to as Catalyst A. For this catalyst, $t_{0.3}$ was 16.8 minutes.

EXAMPLE 2

A silica bound medium crystal size ZSM-5 catalyst, 65% zeolite and 35% silica, was contacted with a solution containing 7.8 weight percent dimethylphenylmethyl polysiloxane (Dow-550) dissolved in decane. The catalyst was calcined at 538° C. in nitrogen followed by air. The catalyst was tested to determine the time required to sorb ortho-xylene in an amount equal to 30% of the total xylene sorption capacity at 120° C. and 4.5±0.8 mm mercury, $t_{0.3}$. This catalyst will be referred to as Catalyst B. For this catalyst, $t_{0.3}$ was 40.3 minutes.

EXAMPLE 3

A silica bound medium crystal size ZSM-5 catalyst, 65% zeolite and 35% silica, was contacted with a solution containing 7.8 weight percent dimethylphenylmethyl polysiloxane (Dow-550) dissolved in decane. The catalyst was calcined at 538° C. in nitrogen followed by air, then was treated with the dimethylphenylmethyl solution again, and solution again, and was calcined a second time. The catalyst was tested to determine the time required to sorb ortho-xylene in an amount equal to 30% of the total xylene sorption capacity at 120° C. and 4.5±0.8 mm mercury, $t_{0.3}$. This catalyst will be referred to as catalyst C. For this catalyst, $t_{0.3}$ was 262 minutes.

EXAMPLE 4

A silica bound medium crystal size ZSM-5 catalyst, 65% zeolite and 35% silica, was treated three times according to the multiple impregnation method with a solution containing 7.8 weight percent dimethylphenylmethyl polysiloxane (Dow-550) dissolved in decane and was calcined between each treatment. The catalyst was tested to determine the time required to sorb ortho-xylene in an amount equal to 30% of the total xylene sorption capacity at 120° C. and 4.5±0.8 mm mercury, $t_{0.3}$. This catalyst will be referred to as catalyst D. For this catalyst, $t_{0.3}$ was 3600 minutes.

EXAMPLE 5

A silica bound medium crystal size ZSM-5 catalyst, 65% zeolite and 35% silica, was treated four times according to the multiple impregnation method with a solution containing 7.8 weight percent dimethylphenylmethyl polysiloxane (Dow-550) dissolved in decane and was calcined between each treatment. The catalyst was tested to determine the time required to sorb ortho-xylene in an amount equal to 30% of the total xylene sorption capacity at 120° C. and 4.5±0.8 mm mercury, $t_{0.3}$. This catalyst will be referred to as catalyst E. For this catalyst, $t_{0.3}$ was 14760 minutes.

EXAMPLE 6

A catalyst containing a medium crystal size ZSM-5 that included 65 weight percent zeolite and 35 weight percent silica binder, was selectivated using a multiple impregnation treatment with four successive impregnations using 7.8 weight percent dimethylphenylmethyl polysiloxane (Dow- 550) dissolved in decane. After each impregnation, the solvent was stripped from the catalyst and the catalyst was calcined in nitrogen and air at 538° C. The catalyst, which was similar to Catalyst E described above, was then platinum exchanged to contain 0.1 weight percent platinum. To prepare this platinum exchanged catalyst, 15 g of the selectivated catalyst was placed in an erlenmeyer flask along with 45 g distilled water and 0.0271 g $Pt(NH_3)_4Cl_2 \cdot H_2O$. The pH of the solution was approximately 3. A drop of 0.1N $NH_4OH$ solution in water was added to the erlenmeyer flask. The pH of the resulting solution increased to about 8. Gently agitating the solution brought the pH down to about 4, at which time another drop of 0.1N $NH_4OH$ was added. This procedure was repeated until the pH of the solution did not drop. The amount of solution required was 0.9 cc (slightly more than the 0.8 cc calculated for complete exchange of Pt). Excess solution was then decanted, the resulting catalyst was washed with water, filtered, washed with about 200 cc of distilled water, and the recovered catalyst was then air dried. This catalyst was calcined at 120° C. for 6 hours under air, followed by slowly ramping the temperature of air calcination at 2° C./min to 350° C., where it was calcined for 2 hours. This catalyst will be referred to as catalyst F.

EXAMPLE 7

A catalyst containing a medium crystal size ZSM-5 that included 65 weight percent zeolite and 35 weight percent silica binder, was selectivated using a multiple impregnation treatment with four successive impregnations using 7.8 weight percent dimethylphenylmethyl polysiloxane (Dow-550) dissolved in decane. After each impregnation, the solvent was stripped from the catalyst and the catalyst was calcined in nitrogen and air at 538° C. The catalyst, which was similar to Catalyst E described above, was then palladium exchanged to contain 0.1 weight percent palladium. To prepare this palladium exchanged catalyst, 15 g of the selectivated catalyst was placed in an erlenmeyer flask along with 45 g distilled water and 0.0375 g $Pd(NH_3)_4Cl_2 \cdot H_2O$. The pH of the solution was approximately 3. A drop of 0.05N $NH_4OH$ solution in water was added to the erlenmeyer flask. The pH of the resulting solution increased to about 8. Gently agitating the solution brought the pH down to about 4, at which time another drop of 0.05N $NH_4OH$ was added. This procedure was repeated until the pH of the solution did not drop. The amount of solution required was 1.6 cc (slightly more than the 1.5 cc calculated for complete exchange of Pd). Excess solution was then decanted, the resulting catalyst was washed with water, filtered, washed with about 200 cc of distilled water, and the recovered catalyst was then air dried. This catalyst was calcined at 120° C. for 6 hours under air, followed by slowly ramping the temperature of air calcination at 2° C./min to 350° C., where it was calcined for 2 hours. This catalyst will be referred to as catalyst G.

EXAMPLE 8

A catalyst containing a medium crystal size ZSM-5 that included 65 weight percent zeolite and 35 weight percent silica binder, was selectivated using a multiple impregnation treatment with four successive impregnations using 7.8 weight percent dimethylphenylmethyl polysiloxane (Dow-550) dissolved in decane. After each impregnation, the solvent was stripped from the catalyst and the catalyst was calcined in nitrogen and air at 538° C. The selectivated catalyst, which was similar to Catalyst E described above, was platinum exchanged in a manner similar to that of Example 6 to contain 0.05 weight percent platinum. This catalyst will be referred to as catalyst H.

EXAMPLE 9

A silica bound zeolite, containing 65 weight percent medium crystal size ZSM-5 and 35 weight percent silica binder, was subjected to a multiple selectivation treatment using three successive impregnations using 7.8 weight percent dimethylphenylmethyl polysiloxane (Dow-550) dissolved in decane. After each impregnation, the solvent was stripped from the catalyst and the catalyst was calcined in nitrogen and air at 538° C. The catalyst, which was similar to Catalyst D described above, was then platinum exchanged in a manner similar to that of Example 6 to contain 0.10 weight percent platinum. This catalyst will be referred to as catalyst I.

EXAMPLE 10

A silica bound zeolite, containing 65 weight percent medium crystal size ZSM-5 and 35 weight percent silica binder, was subjected to a multiple selectivation treatment using two successive impregnations using 7.8 weight percent dimethylphenylmethyl polysiloxane (Dow-550) dissolved in decane. After each impregnation, the solvent was stripped from the catalyst and the catalyst was calcined in nitrogen and air at 538° C. The catalyst, which was similar to Catalyst C described above, was then platinum exchanged in a manner similar to that of Example 6 to contain 0.10 weight percent platinum. This catalyst will be referred to as catalyst J.

EXAMPLE 11

A silica bound zeolite, containing 65 weight percent large crystal size ZSM-5 and 35 weight percent silica binder, was platinum exchanged in a manner similar to that of Example 6 to contain 0.10 weight percent platinum. This catalyst will be referred to as catalyst K. Catalyst K was not selectivated using the multiple impregnation, trim-selectivation, or coke selectivation methods described herein.

EXAMPLE 12

Catalysts F through K were catalytically evaluated for ethylbenzene conversion activity at a hydrogen to hydrocarbon molar ratio of 1 and at 150 psig (1136 kPaa) and at a variety of temperatures and space velocities. The feed used was a mixture of about 60 weight percent meta-xylene, 20 weight percent ortho-xylene, and 20 weight percent ethylbenzene. The catalysts were pretreated at 350° C. for 2 hours in flowing hydrogen before introducing feed. A summary of the results is provided in Tables 1 through 6 below. The molar ratio of benzene formed to ethylbenzene converted is also provided in the following tables. The results indicated in the tables reflect the averages of 2 analyses.

TABLE 1

| Catalyst F | | | | | |
|---|---|---|---|---|---|
| Reaction Conditions | | | | | |
| Temperature, °F. | 760 | 780 | 800 | 820 | 840 |
| Pressure, psig | 150 | 150 | 150 | 150 | 150 |
| $H_2$/HC molar ratio | 1 | 1 | 1 | 1 | 1 |
| WHSV, $hr^{-1}$ | 40 | 40 | 40 | 40 | 40 |

TABLE 1-continued

Catalyst F

| Products, wt. % | | | | | |
|---|---|---|---|---|---|
| $C_5^-$ | 2.21 | 2.72 | 3.53 | 3.09 | 2.98 |
| Benzene | 6.31 | 6.91 | 8.57 | 9.07 | 8.72 |
| Toluene | 0.22 | 0.27 | 0.56 | 0.54 | 0.57 |
| Ethylbenzene | 11.44 | 10.57 | 8.24 | 7.68 | 8.03 |
| Para-xylene | 0.18 | 0.19 | 0.31 | 0.26 | 0.23 |
| Meta-xylene | 59.50 | 59.29 | 58.81 | 59.26 | 59.28 |
| Ortho-xylene | 20.00 | 19.91 | 19.82 | 19.92 | 19.97 |
| C9+ | 0.14 | 0.14 | 0.16 | 0.18 | 0.22 |
| EB Conversion, % | 42.8 | 47.2 | 58.8 | 61.6 | 59.9 |
| Xylene Loss, % | 0.4 | 0.8 | 1.3 | 0.7 | 0.6 |
| Benz./EB mol. ratio | 1.0 | 1.00 | 0.99 | 1.00 | 0.99 |

TABLE 2

Catalyst F

| Reaction Conditions | | | |
|---|---|---|---|
| Temperature, °F. | 760 | 780 | 800 |
| Pressure, psig | 150 | 150 | 150 |
| $H_2$/HC molar ratio | 1 | 1 | 1 |
| WHSV, hr$^{-1}$ | 20 | 20 | 20 |
| Products, wt. % | | | |
| $C_5^-$ | 3.38 | 3.89 | 2.88 |
| Benzene | 8.78 | 9.03 | 10.44 |
| Toluene | 0.34 | 0.43 | 0.72 |
| Ethylbenzene | 7.96 | 7.76 | 6.22 |
| Para-xylene | 0.22 | 0.22 | 0.28 |
| Meta-xylene | 59.22 | 58.77 | 59.42 |
| Ortho-xylene | 19.98 | 19.78 | 19.93 |
| C9+ | 0.12 | 0.12 | 0.11 |
| EB Conversion, % | 60.2 | 61.2 | 68.9 |
| Xylene Loss, % | 0.7 | 1.5 | 0.5 |
| Benz./EB mol. ratio | 0.99 | 1.00 | 1.03 |

TABLE 3

Catalyst F

| Reaction Conditions | | | |
|---|---|---|---|
| Temperature, °F. | 800 | 800 | 800 |
| Pressure, psig | 150 | 150 | 150 |
| $H_2$/HC molar ratio | 1 | 1 | 1 |
| WHSV, hr$^{-1}$ | 15 | 15 | 15 |
| Products, wt.% | | | |
| $C_5^-$ | 4.36 | 4.47 | 3.94 |
| Benzene | 10.54 | 10.66 | 10.58 |
| Toluene | 0.65 | 0.75 | 0.88 |
| Ethylbenzene | 5.58 | 5.37 | 5.25 |
| Para-xylene | 0.24 | 0.23 | 0.22 |
| Meta-xylene | 58.70 | 58.60 | 59.01 |
| Ortho-xylene | 19.83 | 19.83 | 20.03 |
| C9+ | 0.10 | 0.09 | 0.09 |
| EB Conversion, % | 72.1 | 73.2 | 73.8 |
| Xylene Loss, % | 1.5 | 1.7 | 0.9 |
| Benz./EB mol. ratio | 0.99 | 0.99 | 0.97 |

TABLE 4

Catalyst F

| Reaction Conditions | | | | |
|---|---|---|---|---|
| Temperature, °F. | 780 | 800 | 820 | 840 |
| Pressure, psig | 150 | 150 | 150 | 150 |

TABLE 4-continued

Catalyst F

| $H_2$/HC molar ratio | 1 | 1 | 1 | 1 |
|---|---|---|---|---|
| WHSV, hr$^{-1}$ | 10 | 10 | 10 | 10 |
| Products, wt. % | | | | |
| $C_5^-$ | 4.91 | 4.74 | 4.33 | 4.68 |
| Benzene | 11.26 | 11.46 | 11.27 | 11.44 |
| Toluene | 0.77 | 0.98 | 1.14 | 1.36 |
| Ethylbenzene | 4.53 | 4.26 | 4.22 | 4.02 |
| Para-xylene | 0.28 | 0.26 | 0.27 | 0.25 |
| Meta-xylene | 58.41 | 58.46 | 58.77 | 58.33 |
| Ortho-xylene | 19.75 | 19.75 | 19.91 | 19.83 |
| C9+ | 0.09 | 0.09 | 0.09 | 0.09 |
| EB Conversion, % | 77.4 | 78.7 | 78.9 | 79.9 |
| xylene Loss, % | 2.0 | 1.9 | 1.3 | 2.0 |
| Benz./EB mol. ratio | 0.99 | 0.99 | 0.97 | 0.97 |

TABLE 5

| Catalyst | F | G | H | I | J | K |
|---|---|---|---|---|---|---|
| Reaction Conditions | | | | | | |
| Temp. °F. | 800 | 800 | 800 | 800 | 800 | 800 |
| Pres., psig | 150 | 150 | 150 | 150 | 150 | 150 |
| $H_2$/HC mol ratio | 1 | 1 | 1 | 1 | 1 | 1 |
| WHSV, hr$^{-1}$ | 20 | 20 | 20 | 20 | 20 | 20 |
| Products, wt. % | | | | | | |
| $C_5^-$ | 2.88 | 1.47 | 2.77 | 3.22 | 5.86 | 3.56 |
| Benzene | 10.44 | 4.41 | 10.14 | 9.57 | 10.63 | 9.83 |
| Toluene | 0.72 | 0.39 | 1.35 | 0.76 | 11.03 | 2.91 |
| Ethylbenzene | 6.22 | 13.32 | 5.57 | 6.60 | 1.35 | 5.39 |
| Para-xylene | 0.28 | 0.35 | 0.68 | 5.29 | 9.83 | 16.95 |
| Meta-xylene | 59.42 | 59.21 | 59.30 | 55.17 | 43.27 | 42.46 |
| Ortho-xylene | 19.93 | 19.86 | 20.02 | 19.20 | 17.39 | 17.95 |
| C9+ | 0.11 | 0.99 | 0.17 | 0.19 | 0.64 | 0.95 |
| EB Conv., % | 68.9 | 33.4 | 72.2 | 67.0 | 93.3 | 73.1 |
| Xylene Loss, % | 0.5 | 0.7 | 0.0 | 0.4 | 11.9 | 3.3 |
| Benz./EB mol ratio | 1.03 | 0.90 | 0.95 | 0.97 | 0.77 | 0.91 |

EXAMPLE 13

A xylene isomerization evaluation was conducted using a first bed containing Catalyst I and a second bed containing an alumina bound small crystal ZSM-5 (65 weight percent zeolite and 35 weight percent binder) that has been impregnated with 0.1 weight percent Pt and has been steamed to an alpha of about 13. In this evaluation, the first and second beds each represented 50 weight percent of the total catalyst loading. The feed for the evaluation consisted of 9 weight percent ethylbenzene, 65 weight percent meta-xylene, 24 weight percent ortho-xylene, and 1 weight percent para-xylene. The evaluation was conducted at 781° F. (416.1° C.), 200 psig (1480 kPaa), a 1 hydrogen to hydrocarbon molar ratio and a 10 weight hourly space velocity (WHSV) based upon the total catalyst loading. Results of this evaluation are shown in Table 6.

EXAMPLE 14

A xylene isomerization evaluation was conducted using a first bed containing Catalyst K and a second bed containing an alumina bound small crystal ZSM-5 (65 weight percent zeolite and 35 weight percent binder) that has been impregnated with 0.1 weight percent Pt and has been steamed to an alpha of about 13. In this evaluation, the first bed represented 25 weight percent and the second bed represented 75 weight percent of the total catalyst loading. The feed for the evaluation consisted of 8.9 weight percent ethylbenzene, 65.4 weight percent meta-xylene, 24.5 weight percent ortho-xylene, and 1.2 weight percent para-xylene. The evaluation was conducted at 781° F. (416.1° C.), 200 psig (1480 kPaa), a 1 hydrogen to hydrocarbon molar ratio and a 10 weight hourly space velocity (WHSV) based upon the total catalyst loading. Results of this evaluation are shown in Table 6.

TABLE 6

| Top Bed Catalyst | | I | K |
|---|---|---|---|
| Top Bed Catalyst, wt. % | | 50 | 25 |
| Bottom Bed Catalyst, wt. % | | 50 | 75 |
| Concentration, wt. % | Feed | Products | |
| $C_5^-$ | | 1.95 | 2.13 |
| Benzene | | 4.10 | 3.74 |
| Toluene | | 1.32 | 2.09 |
| Ethylbenzene | 8.9 | 2.27 | 2.33 |
| Para-xylene | 1.2 | 21.35 | 21.28 |
| Meta-xylene | 65.4 | 47.44 | 46.55 |
| Ortho-xylene | 24.5 | 20.89 | 20.46 |
| $C9^+$ | | 0.67 | 1.43 |
| EB Conversion, % | | 74.4 | 73.8 |
| Xylene Loss, % | | 1.5 | 3.0 |
| Para-xylene approach to equilibrium | | 101.5 | 102.9 |

What we claim is:

1. A process for isomerizing xylenes in a feed comprising ethylbenzene and xylenes, comprising the steps of:
   (a) contacting the feed under ethylbenzene conversion conditions with a first bed of a first catalyst comprising an intermediate pore size zeolite having a constraint index ranging from 1 to 12 and a silica to alumina ratio of at least about 5, said intermediate pore size zeolite having been modified by being exposed to at least one selectivation sequence that comprises the steps of contacting the zeolite with a organosilicon selectivating agent to obtain a selectivated zeolite and subsequently calcining the selectivated zeolite, to form an ethylbenzene depleted product; and
   (b) contacting the ethylbenzene depleted product under xylene isomerization conditions with a second bed of a second catalyst comprising an intermediate pore size zeolite, wherein the second catalyst requires less than 50 minutes to sorb ortho-xylene in an amount equal to 30% of the equilibrium sorption capacity for xylenes at 120° C. and at a xylene partial pressure of 4.5±0.8 mm of mercury.

2. The process according to claim 1, wherein the ethylbenzene conversion conditions comprise a temperature of from about 400° F. to about 1,000° F., a pressure of from about 0 to 1,000 psig, a weight hourly space velocity (WHSV) of between 0.5 and 100 hr$^{-1}$, and a H$_2$/HC mole ratio of between about 0.1 and about 10.

3. The process according to claim 1, wherein the first catalyst further comprises a silica binder.

4. The process according to claim 1, wherein the first catalyst comprises ZSM-5 or silica bound ZSM-5.

5. The process according to claim 4, wherein the selectivating agent comprises dimethylphenylmethyl polysiloxane.

6. The process according to claim 4, wherein the intermediate pore size zeolite of the first catalyst has been modified by being exposed to at least three selectivation sequences.

7. The process according to claim 6, wherein the ZSM-5 of the first catalyst has an average crystal size of from about 0.1 to about 1µ.

8. The process according to claim 7, wherein the first catalyst contains no intentionally added alumina.

9. The process according to claim 8, wherein the first catalyst further comprises a hydrogenation-dehydrogenation component selected from Group VIIIA, Group VIIA, Group VIA, Group VB, Group IVB, Group IIIB, Group IB or combinations thereof of the Periodic Table.

10. The process according to claim 9, wherein the hydrogenation-dehydrogenation component is selected from the group consisting of Fe, Co, Ni, Ru, Rh, Pd, Os, Ir, Pt, Mn, Re, Cu, Ag, Au, Cr, Mo, W, Ga, In, Bi and combinations thereof.

11. The process according to claim 10, wherein the hydrogenation-dehydrogenation component consists essentially of Pt.

12. The process according to claim 5, wherein the selectivating agent for the first catalyst comprises silicon and wherein the first catalyst comprises at least 9 weight percent silicon exclusive of any silicon present in a binder or in the zeolite.

13. The process according to claim 12, wherein the first catalyst comprises at least 0.03 weight percent alkali metal or alkaline earth metal exclusive of any alkali metal or alkaline earth metal present from the synthesis of the zeolite.

14. The process according to claim 13, wherein the first catalyst has been treated to contain the alkali metal or the alkaline earth metal by contacting the first catalyst with an aqueous solution of the alkali metal or the alkaline earth metal, washing the treated first catalyst with water, and drying the treated and washed first catalyst.

15. The process according to claim 12, wherein the first catalyst has been steamed.

16. The process according to claim 1, wherein the first catalyst comprises zeolite HZSM-5 and said selectivation sequence comprises trim-selectivating by contacting the HZSM-5 with an organosilicon compound in an aromatic or paraffinic hydrocarbon carrier under conditions effective to deposit the organosilicon compound on the zeolite while preventing excessive aging of the catalyst.

17. The process according to claim 16, wherein the trim-selectivation is further carried out in the presence of hydrogen in a mole ratio of hydrogen to hydrocarbon in the aromatic or paraffinic feedstock of about 0.1 to 20, and the trim-selectivation conditions comprise a temperature of about 100° C. to about 600° C., a pressure ranging from about 0 to about 2000 psig, and a weight hourly space velocity (WHSV) from about 0.1 to about 100 hr$^{-1}$.

18. The process according to claim 1, wherein the second catalyst comprises an intermediate pore size zeolite selected from the group consisting of ZSM-5, ZSM-11, ZSM-12, ZSM-21, ZSM-22, ZSM-23, ZSM-35, ZSM-38, ZSM-48, ZSM-57, and ZSM-58.

19. The process according to claim 1, wherein the xylene isomerization conditions comprise a temperature of from about 400° F. to about 1,000° F., a pressure of from about 0 to 1,000 psig, a weight hourly space velocity (WHSV) of between 0.5 and 100 hr$^{-1}$, and a H$_2$/HC mole ratio of between about 0 and about 10.

20. A process for aromatics production from a feed comprising ethylbenzene and at least one xylene, the process comprising the steps of:
   (a) contacting the feed with a first catalyst under ethylbenzene conversion conditions to thereby produce an ethylbenzene depleted product, the first catalyst being effective to produce less than 12 weight % para-xylene when tested by contacting a test feed containing 60 weight % meta-xylene, 20 weight % ortho-xylene and 20 weight % ethylbenzene at a temperature of 800° F., a pressure of 150 psig, a weight hourly space velocity of 20 hr$^{-1}$, and a hydrogen to hydrocarbon molar ratio of 1; and (b) contacting the ethylbenzene depleted product with a second catalyst under xylene isomerization conditions.

21. The process according to claim 20, wherein the ethylbenzene conversion conditions comprise a temperature of from about 400° F. to about 1,000° F., a pressure of from about 0 to 1,000 psig, a weight hourly space velocity (WHSV) of between 0.5 and 100 hr$^{-1}$, and a H$_2$/HC mole ratio of between about 0.1 and about 10.

22. The process according to claim 20, wherein the first catalyst comprises an intermediate pore size zeolite.

23. The process according to claim 20, wherein the first catalyst has been selectivated by a method selected from the group consisting of multiple impregnation of the catalyst with a silicon compound, trim-selectivation of the catalyst with a silicon compound, and coke selectivation.

24. The process according to claim 23, wherein the first catalyst comprises ZSM-5.

25. The process according to claim 24, wherein the first catalyst further comprises silica bound ZSM-5 that has been modified by being exposed to at least one selectivation sequence, the selectivation sequence comprising the steps of contacting the zeolite with a selectivating agent and subsequently calcining the selectivated zeolite.

26. The process according to claim 25, wherein the selectivating agent comprises dimethylphenylmethyl polysiloxane.

27. The process according to claim 25, wherein the silica bound ZSM-5 of the first catalyst has been modified by being exposed to at least three selectivation sequences.

28. The process according to claim 25, wherein the first catalyst is silica bound by the steps of:

(a) mulling and then extruding a mixture comprising water, ZSM-5, colloidal silica and sodium ions under conditions sufficient to form an extrudate having an intermediate green strength sufficient to resist attrition during ion exchange step (b) set forth hereinafter;

(b) contacting the uncalcined extrudate of step (a) with an aqueous solution comprising ammonium cations under conditions sufficient to exchange cations in said ZSM-5 with ammonium cations; and (c) calcining the ammonium exchanged extrudate of step (b) under conditions sufficient to generate the hydrogen form of said ZSM-5 and increase the crush strength of said extrudate; wherein the selectivation sequence for the silica bound catalyst comprises the following steps:

(d) contacting the calcined extrudate of step (c) with a liquid comprising a liquid carrier and at least one organosilicon selectivating agent having at least two silicon atoms per molecule under conditions sufficient to incorporate said organosilicon selectivating agent in the extrudate, (e) calcining the extrudate of step (d) under conditions sufficient to decompose said organosilicon selectivating agent and to remove any residue of said liquid carrier from said extrudate; and (f) repeating selectivation steps (d) and (e) at least once.

29. The process according to claim 25, wherein the ZSM-5 of the first catalyst has an average crystal size of from about 0.1 to about 1μ.

30. The process according to claim 29, wherein the first catalyst contains no intentionally added alumina.

31. The process according to claim 30, wherein the first catalyst further comprises a hydrogenation-dehydrogenation component selected from Group VIIIA, Group VIIA, Group VIA, Group VB, Group IVB, Group IIIB, Group IB or combinations thereof of the Periodic Table.

32. The process according to claim 31, wherein the hydrogenation-dehydrogenation component is selected from the group consisting of Fe, Co, Ni, Ru, Rh, Pd, Os, Ir, Pt, Mn, Re, Cu, Ag, Au, Cr, Mo, W, Ga, In, Bi and combinations thereof.

33. The process according to claim 32, wherein the hydrogenation-dehydrogenation component consists essentially of Pt.

34. The process according to claim 23 wherein the first catalyst has been coke selectivated.

35. The process according to claim 23 wherein the first catalyst comprises zeolite HZSM-5 that has been trim-selectivated by contacting the zeolite with an organosilicon compound in an aromatic or paraffinic carrier under conditions effective to deposit the organosilicon compound on the zeolite while preventing excessive aging of the catalyst.

36. The process according to claim 35, wherein the trim-selectivation is further carried out in the presence of hydrogen in a mole ratio of hydrogen to hydrocarbon in the aromatic or paraffinic feedstock of about 0.1 to 20, and the trim-selectivation conditions comprise a temperature of about 100° C. to about 600° C., a pressure ranging from about 0 to about 2000 psig, and a weight hourly space velocity (WHSV) from about 0.1 to about 100 hr$^{-1}$.

37. The process according to claim 23, wherein the first catalyst comprises coke selectivated large crystal size ZSM-5.

38. The process according to claim 23, wherein the first catalyst comprises a lobed shape.

39. The process according to claim 20, wherein the ethylbenzene depleted product contains less than 85 weight percent of the ethylbenzene present in the feed and wherein the first catalyst is further effective when tested to convert at least 15 weight percent of the ethylbenzene present in the test feed containing 60 weight % meta-xylene, 20 weight % ortho-xylene, and 20 weight % ethylbenzene while producing less than 10 weight percent C$_5^-$ products when contacting the test feed at the temperature of 800° F., the pressure of 150 psig, the weight hourly space velocity of 20 hr$^{-1}$, and the hydrogen to hydrocarbon molar ratio of 1.

40. The process according to claim 39, wherein the first catalyst is effective when tested to produce less than 6 weight % para-xylene when contacting a test feed containing 60 weight % meta-xylene, 20 weight % ortho-xylene and 20 weight % ethylbenzene at a temperature of 800° F., a pressure of 150 psig, a weight hourly space velocity of 20 hr$^{-1}$, and a hydrogen to hydrocarbon molar ratio of 1.

41. The process according to claim 20, wherein the second catalyst comprises an intermediate pore size zeolite selected from the group consisting of ZSM-5, ZSM-11, ZSM-12, ZSM-21, ZSM-22, ZSM-23, ZSM-35, ZSM-38, ZSM-48, ZSM-57, and ZSM-58.

42. The process according to claim 20, wherein the xylene isomerization conditions comprise a temperature of from about 400° F. to about 1,000° F., a pressure of from about 0 to 1,000 psig, a weight hourly space velocity (WHSV) of between 0.5 and 100 hr$^{-1}$, and a H$_2$/HC mole ratio of between about 0 and about 10.

* * * * *